United States Patent

Bank et al.

[11] Patent Number: 5,136,071
[45] Date of Patent: Aug. 4, 1992

[54] SODIUM BOROHYDRIDE AS ACTIVATOR FOR PHENYLBORANE CATALYZED DISPROPORTIONATION OF ARYLSILANES

[75] Inventors: Howard M. Bank, Freeland; Terrence K. Hilty, Midland, both of Mich.

[73] Assignee: Dow Corning Corporation, Midland, Mich.

[21] Appl. No.: 808,343

[22] Filed: Dec. 16, 1991

[51] Int. Cl.$^5$ ................................................ C07F 7/08
[52] U.S. Cl. ........................................................ 556/469
[58] Field of Search ........................................ 556/469

[56] References Cited

U.S. PATENT DOCUMENTS

| | | | |
|---|---|---|---|
| 2,611,775 | 9/1952 | Barry | 556/469 X |
| 2,626,266 | 1/1953 | Barry | 556/469 |
| 2,626,267 | 1/1953 | Barry | 556/469 |
| 2,627,451 | 2/1953 | Erickson et al. | 556/469 X |
| 2,647,912 | 8/1953 | Barry et al. | 556/469 |
| 2,746,981 | 4/1956 | Wagner | 556/469 |

FOREIGN PATENT DOCUMENTS 263189  4/1986  Japan.

OTHER PUBLICATIONS

Wright, The Role of Boron Trichloride in the Synthesis of Phenyltrichlorosilane. . . J. Organomet. Chem. 145:307–314 (1978).

Primary Examiner—Paul F. Shaver
Attorney, Agent, or Firm—William F. Boley

[57] ABSTRACT

The present invention is a process for the disproportionation of arylsilanes using a phenylborane as a catalyst. The process uses sodium borohydride to activate the phenylborane catalyst, thereby reducing the induction time associated with the use of the phenylborane catalyst. The present process is especially useful for the disproportionation of phenyldichlorosilane to diphenyldichlorosilane and dichlorosilane.

14 Claims, No Drawings

SODIUM BOROHYDRIDE AS ACTIVATOR FOR PHENYLBORANE CATALYZED DISPROPORTIONATION OF ARYLSILANES

BACKGROUND OF INVENTION

The present invention is a process for the disproportionation of arylsilanes using a phenylborane as a catalyst. The process uses sodium borohydride to activate the phenylborane catalyst, thereby reducing the induction time associated with the use of the phenylborane catalyst. The present process is especially useful for the disproportionation of phenyldichlorosilane to diphenyldichlorosilane and dichlorosilane.

It is known that Friedel-Crafts type catalysts taken from the group consisting of aluminum and boron chloride can catalyze the addition of benzene to trichlorosilane. For example, Barry, U.S. Pat. No. 2,626,266, issued Jan. 20, 1953, describes a process for reacting a benzenoid hydrocarbon with trichlorosilane in the presence of a boron halide to form a benzenoid substituted chlorosilane. In addition, Barry, U.S. Pat. No. 2,626,267, issued Jan. 20, 1953, describes the use of aluminum chloride to catalyze the addition of a benzenoid hydrocarbon to trichlorosilane.

Wright, J. Organomet. Chem. 145: 307-314, 1978, suggests that phenylborane catalysts may be superior to boron halide catalysts for the addition of benzene to trichlorosilane.

Wagner, U.S. Pat. No. 2,746,981, issued May 22, 1956, teaches the preparation of diaryldichlorosilanes by heating monoaryldichlorosilanes in the presence of a Friedel-Crafts type catalyst taken from the group consisting of aluminum or boron chloride.

Japanese Patent No. 263189, Pub. 1987, teaches a process where arylboranes, for example, triphenylborane is used to catalyze the disproportionation of aryldihalosilanes under conditions of reduced pressure. Running the process at reduced pressure is reported to increase the yield of diarylhalosilane.

Generally, aluminum halides have been preferred as a catalyst for the disproportionation of arylhalosilanes. The reason for this preference is the apparent faster rate of reaction associated with aluminum halide as compared to boron halides. However, aluminum halide catalysts have disadvantages in that (1) the aluminum halide must be deactivated before products can be distilled, (2) the aluminum halide can contaminate the process with aluminum salts, and (3) the aluminum halide leaves a solid-liquid distillation residue. Since phenylborane compounds are soluble in the arylsilanes used in the disproportionation process, their use could alleviate problems described with the use of aluminum halide catalysts. However, phenylborane compounds demonstrate a latent period before the disproportionation reaction occurs, thus extending the time required for disproportionation to occur.

The inventors have found that sodium borohydride can activate phenylborane compounds, thereby reducing the latent period and making the phenylborane compounds more desirable as catalysts for the disproportionation of arylsilanes.

SUMMARY OF INVENTION

The present invention is a process for the disproportionation of arylsilanes using a phenylborane as a catalyst. The process uses sodium borohydride to activate the phenylborane catalyst, thereby reducing the induction time associated with the use of the phenylborane catalyst. The present process is especially useful for the disproportionation of phenyldichlorosilane to diphenyldichlorosilane and dichlorosilane.

DESCRIPTION OF INVENTION

The present invention is a process for the disproportionation of arylsilanes. The process comprises (A) forming a mixture comprising arylsilanes of formula $$R_a R^1_b H_c SiX_{4-a-b-c}, \quad (1)$$

a phenylborane catalyst of formula $$Ph_n BX_{3-n}, \quad (2)$$

and sodium borohydride activator, where concentration of the phenylborane catalyst is sufficient to increase the rate of disproportionation of the arylsilanes and concentration of sodium borohydride is sufficient to reduce induction time for the process;

(B) heating the mixture to a temperature within a range of about 70° C. to 170° C.; and (C) recovering product silanes of formula $$R_{a+1} R^1_b H_{c-1} SiX_{4-a-b-c} \text{ and} \quad (3)$$

$$R_{a-1} R^1_b H_{c+1} SiX_{4-a-b-c}; \quad (4)$$

where each R is independently selected from a group consisting of aryls and substituted aryls, $R^1$ is selected from a group consisting of alkyls of one to 20 carbon atoms, X is a halogen selected from a group consisting of bromine, chlorine, and iodine, Ph is phenyl, $a=1, 2,$ or $3$, $b=0, 1,$ or $2$, $c=1, 2$ or $3$, $a+b+c=2, 3,$ or $4$, and $n=1, 2,$ or $3$.

Arylsilanes which can be disproportionated by the present process are described by formula (1). The arylsilane can contain one, two, or three R substituents, where each R is a radical independently selected from a group consisting of aryls and substituted aryls. By "substituted aryl" it is meant that one or more of the carbons forming the cyclic ring is substituted with a substituent selected from a group consisting of alkyls of one to 20 carbon atoms; haloalkyls of one to 20 carbon atoms; and halogens. The radical R can be, for example, phenyl, biphenyl, naphthyl, tolyl, xylyl, isopropylphenyl, chlorophenyl, dichlorophenyl, and fluorophenyl. Preferred is when R is phenyl.

The arylsilane can contain zero, one, or two substituents $R^1$, where $R^1$ is an alkyl radical of one to 20 carbon atoms. The radical $R^1$ can be, for example, methyl, ethyl, propyl, isopropyl, butyl, tert-butyl, and decyl. Preferred is when $R^1$ is methyl.

The arylsilane must contain at least one hydrogen bonded to the silicon atom and can contain a maximum of three hydrogen atoms bonded to the silicon atom. It is preferred that the arylsilane contain one hydrogen bonded to the silicon atom.

The arylsilane can contain zero, one, or two halogens, X, where the halogen is selected from a group consisting of bromine, chlorine, and iodine. The preferred halogen, for X, is chlorine.

The arylsilane can be, for example, phenyldichlorosilane, phenylchlorosilane, phenyldibromosilane, phenyldiiodosilane, tolyldichlorosilane, chlorophenyldichlorosilane, methylphenylchlorosilane, ethylphenylchlorosilane, triphenylsilane, and phenylsilane.

The phenylborane catalysts useful in the present process are described by formula (2). The phenylborane catalyst can have zero, one, or two halogens, X, bound to the boron atom, where X is selected from a group consisting of bromine, chlorine, and iodine. The preferred halogen is chlorine. The phenylborane catalyst must contain at least one phenyl substituent and may contain as many as three phenyl substituents. Preferred is when the phenylborane catalyst is triphenylborane.

A concentration of phenylborane catalyst sufficient to increase the rate of disproportionation of the arylsilanes is added to the mixture. A preferred concentration of phenylborane catalyst is about 0.1 to 5.0 weight percent of the weight of arylsilanes added to the process. More preferred is when the concentration of the phenylborane catalyst is about 1.0 to 2.0 weight percent of the weight of arylsilanes added to the process.

Sodium borohydride, $NaBH_4$, is added to the process as an activator for the phenylborane catalyst. By "activator" is meant the sodium borohydride reduces the induction time associated with the phenylborane catalyzed disproportionation of arylsilanes. Therefore, the concentration of sodium borohydride added to the process can be any concentration sufficient to reduce the induction time for the process. The sodium borohydride is added to the process as a solid in the form of, for example, powder, chips, flakes, granules, and pellets. Preferred is when the sodium borohydride has a particle size greater than about 100 microns in diameter. More preferred is when the sodium borohydride has a particle size within a range of about 1 mm to 12 mm in diameter.

The present process can be run as a continuous process or as a batch process in standard type reactors for running such processes. Since the sodium borohydride is present in the process as a solid, it is possible to form, for example, a packed-bed, fluidized-bed, or stirred-bed of the sodium borohydride and pass a mixture of the phenylborane catalyst and arylsilanes through the bed to effect disproportionation of the arylsilanes. The present process can also be run as a batch process in a stirred-tank reactor. When the process is run as a batch process, a concentration of sodium borohydride within a range of about 0.05 to 10 weight percent of the weight of the arylsilanes added to the process is preferred. More preferred is a concentration of sodium borohydride within the range of about 0.1 to 2.0 weight percent of the weight of the arylsilanes added to the process.

The mixture comprising the arylsilanes, phenylborane catalyst, and sodium borohydride activator is heated to a temperature within a range of about 70° C. to 170° C. to effect disproportionation of the arylsilanes. More preferred is when the temperature is within a range of about 100° C. to 150° C.

The length of time required to heat the mixture to effect disproportionation of the arylsilanes will depend upon the temperature, the particular arylsilanes, and the particular phenylborane catalyst employed in the process. In general, heating times of about 0.5 minutes to 18 hours are considered useful. Preferred are heating times of about 15 minutes to one hour.

The present process can be run under standard, reduced, or elevated pressures. Preferred is when the process is run at reduced pressure. By "reduced pressure" is meant a pressure less than a standard pressure of about 760 mmHg. In the described process, two arylsilane molecules disproportionate effecting an exchange of an R substituent of one arylsilane for a hydrogen on the silicon atom of the other arylsilane. The result of this disproportionation reaction is a product silane molecule containing an added R substituent and a second low-boiling product silane containing an additional hydrogen. The inventors believe that the arylsilanes and product silanes form an equilibrium mixture. Therefore by removing the second low-boiling silane as it is formed, process yield of the silane products containing an added R substituent is improved.

Product silanes of formula (3) and formula (4) are recovered from the process. The method of recovery of the product silanes depends upon whether the process is run as a continuous process or a batch process. When the process is run as a continuous process, recovery of the product silanes can be effected by, for example, distillation. When the process is run as a batch process, separation of the solid sodium borohydride from the product silanes can be effected by standard methods for separating solids from liquids, for example, filtration or settling. The separated liquid can then be distilled to recover product silanes.

The product silanes can be, for example, diphenyldichlorosilane, triphenylchlorosilane, diphenyldibromosilane, diphenyldiiodosilane, ditolyldichlorosilane, di(chlorophenyl) dichlorosilane, methyldiphenylchlorosilane, ethyldiphenylchlorosilane, dichlorosilane, trichlorosilane, diphenylchlorosilane, methylchlorosilane, ethylchlorosilane, diphenylsilane, and tetraphenylsilane.

The following examples are provided to illustrate the present invention. These examples are not intended to limit the present claims.

EXAMPLE 1

(Not within the scope of the present invention)

The ability of triphenylborane to effect disproportionation of phenyldichlorosilane at reduced pressure was evaluated. The evaluation was conducted in a 300-ml three-neck flask containing a magnetic stirring bar. Prior to use, the flask was washed in a caustic bath, rinsed with water, and dried overnight at 120° C. The dried flask was capped hot, cooled, and placed in an argon-purged dry bag. The flask was then opened and 60.0 g of phenyldichlorosilane and 0.73 g of triphenylborane added. The triphenylborane dissolved immediately giving a clear solution. The flask was connected through a cold trap to a vacuum source. The flask was purged with nitrogen and the flask contents heated at about 135° C., at a pressure of about 140 mmHg, for 2.5 hours, at which time the flask contents changed color and product begin to collect in the cold trap. After 3.0 hours, heating of the flask contents was stopped and the flask contents cooled. The cold trap contained 13.3 g (77.7% yield) of dichlorosilane.

Analysis of the content of the flask was conducted using gas liquid chromatography (GLC) with a thermal conductivity (TC) detector. The results are presented in Table 1 as the percent area (area %) under the trace defined by the GLC-TC analysis, for the listed compounds.

TABLE 1

Triphenylborane Catalyzed Disproportionation of
Phenyldichlorosilane at Reduced Pressure

| | | | GLC-TC Area % | | | |
|---|---|---|---|---|---|---|
| $HSiCl_3$ | $PhH_2SiCl$ | $PhSiCl_2$ | $PhSiCl_3$ | $Ph_2HSiCl$ | $Ph_2SiCl_2$ | $Ph_3SiCl$ |
| 0 | 0.18 | 12.32 | 8.61 | 1.11 | 73.3 | 1.55 |

EXAMPLE 2

The ability of sodium borohydride to activate the triphenylborane catalyzed disproportionation of phenyldichlorosilane was evaluated. The reaction flask was prepared and purged as described for Example 1. A mixture of 61.5 g phenyldichlorosilane, 0.80 g triphenylborane, and 0.50 g sodium borohydride ($NaBH_4$) was formed in the flask. The sodium borohydride was in the form of 8.0 mm pellets purchased from Morton Thiokol, Danvers, Mass. The triphenylborane was purchased from Johnson Matthey, Ward Hill, Mass. The mixture was heated to about 130° C., at a pressure of about 140 mmHg, for about 5 minutes, at which time the mixture developed a yellow color and product begin to collect in the cold trap. The mixture was allowed to cool to 98° C., at 60 mmHg, and dichlorosilane was evolved over a 25 minute period, after which a sample was taken for analysis (Labelled as S-1). At this time the cold trap contained 11.5 g (65.5% yield) of dichlorosilane. Heating of the mixture was then continued for about another one hour in the absence of sodium borohydride, the mixture cooled, and a second sample (Labeller as S-2) taken for analysis. The samples taken from the flask were analyzed by GLC-TC, as described for Example 1. The results are given in Table 2 as the percent area under the GLC-TC trace, for each of the listed compounds.

TABLE 2

Sodium Borohydride Activation of The Triphenylborane
Catalyzed Disproportionation of Phenyldichlorosilane
at Reduced Pressure

| | | | | GLC-TC Area % | | | |
|---|---|---|---|---|---|---|---|
| | $HSiCl_3$ | $PhH_2SiCl$ | $PhHSiCl_2$ | $PhSiCl_3$ | $Ph_2HSiCl$ | $Ph_2SiCl_2$ | $Ph_3SiCl$ |
| S-1 | 0.00 | 0.22 | 21.57 | 7.63 | 0.62 | 66.94 | 0.39 |
| S-2 | 0.00 | 0.08 | 8.65 | 9.19 | 0.72 | 77.66 | 1.31 |

The results of Example 2, when contrasted with the results of Example 1, demonstrate that sodium borohydride significantly reduces the induction period associated with the triphenylborane catalyzed disproportionation of phenyldichlorosilane.

EXAMPLE 3

The ability of sodium borohydride to activate the triphenylborane catalyzed disproportionation of phenyldichlorosilane was evaluated in sealed tubes. The evaluation was conducted in sealed, 8 mm by 25 cm Pyrex Brand tubes. Prior to sealing and use, the Pyrex tubes were dried in an oven at 140° C. for 16 hours. The tubes were then removed from the oven, purged with argon, and placed in an argon-purged bag where 2.0 ml of phenyldichlorosilane was added to the tube. The concentrations of triphenylborane and sodium borohydride added to each tube is presented in Table 3. The concentrations are given as a weight percent (Wt %) of the weight of phenyldichlorosilane added to the process. The sodium borohydride, as described in Example 2, was in the form of crushed 8.0 mm pellets having an average particle size of about 1.0 mm or greater. The tubes were sealed and placed in a tube furnace for one hour at 130° C. At the end of one hour, the tubes were cooled and the contents analyzed by GLC-TC. The results are presented in Table 3 as the percent area under the GLC-TC trace for each of the listed compounds.

TABLE 3

Sodium Borohydride Activation of The Triphenylborane
Disproportionation of Phenyldichlorosilane in Sealed Tubes

| Catalyst | Activator | GLC-TC Area % | | | | |
|---|---|---|---|---|---|---|
| (Wt % $Ph_3B$) | (Wt % $NaBH_4$) | $PhH_2SiCl$ | $PhHSiCl_2$ | $PhSiCl_3$ | $Ph_2HSiCl$ | $Ph_2SiCl_2$ |
| — | — | 0.00 | 96.17 | 2.22 | 0.08 | 0.00 |
| — | 0.3 | 0.00 | 97.04 | 2.53 | 0.03 | 0.16 |
| — | 1.1 | 0.00 | 97.07 | 3.01 | 0.02 | 0.12 |
| 1.3 | — | 0.00 | 96.10 | 2.80 | 0.00 | 0.08 |
| 1.3 | 0.3 | 0.10 | 31.66 | 7.36 | 0.64 | 56.76 |
| 1.3 | 1.1 | 0.75 | 49.59 | 3.95 | 0.70 | 32.91 |

EXAMPLE 4

(Not within the scope of the present invention.)

The ability of sodium borohydride to activate tricyclohexylborane as a catalyst for the disproportionation of phenyldichlorosilane was evaluated. A mixture consisting of 2.0 ml of phenyldichlorosilane, 0.3 g (1.3 Wt %) tricyclohexylborane, and 0.02 g (1.0 Wt %) of crushed 8.0 mm sodium borohydride pellet was formed in a tube prepared as described in Example 3. The tube was sealed and heated for one hour at 130° C. At the end of one hour, the tube was cooled and the content of the tube was analyzed by GLC-TC. The results are presented in Table 4 as the percent area under the GLC-TC trace for each of the listed compounds.

TABLE 4

Sodium Borohydride Activation of The Tricyclohexylborane
Catalyzed Disproportionation of Phenyldichlorosilane
at Reduced Pressure

| | | | GLC-TC Area % | | | |
|---|---|---|---|---|---|---|
| $HSiCl_3$ | $PhH_2SiCl$ | $PhHSiCl_2$ | $PhSiCl_3$ | $Ph_2HSiCl$ | $Ph_2SiCl_2$ | $Ph_3SiCl$ |
| 0.00 | 0.00 | 95.00 | 2.63 | 0.50 | 0.00 | — |

The data given in Table 4 demonstrates that tricyclohexylborane is not activated by sodium borohydride to effect disproportionation of phenyldichlorosilane.

EXAMPLE 5

(Not within the scope of the present invention.)

Boric acid, decaborane, and calcium hydride were evaluated for their ability to activate the triphenylborane catalyzed disproportionation of phenyldichlorosilane. The process was conducted in sealed tubes as described for Example 3. A mixture consisting of 2.0 ml of phenyldichlorosilane, the material to be tested as an activator, and triphenylborane was formed in a tube. The concentrations of the material to be tested as an activator and of triphenylborane are given in Table 5. The concentration of the material to be tested as an activator is expressed as a weight percent of phenyldichlorosilane added to the tube. The concentration of triphenylborane was 1.5 weight percent of the weight of the phenyldichlorosilane. The sealed tubes were heated for one hour at 130° C., cooled, and the content of each tube analyzed by either GLC-TC or GLC with a flame ionization detector (GLC-FID). The results are given in Table 5 as the percent area under the trace defined by GLC-FID or GLC-TC for each of the listed compounds.

TABLE 5

Activation of The Triphenylborane Catalyzed
Disproportionation of Phenyldichlorosilane

| Activator | Wt % | Area % | | | | |
|---|---|---|---|---|---|---|
| | | $HSiCl_3$ | $PhH_2SiCl$ | $PhHSiCl_2$ | $Ph_2SiCl_2$ | $C_6H_6$ |
| $B_{10}H_{14}$ | 1.36 | 0.00 | 0.00 | 90.00 | 0.00 | 2.58 |
| $H_3BO_3$ | 0.91 | 0.00 | 0.00 | 84.20 | 0.00 | 9.60 |
| $CaH_2$ | 4.09 | 0.00 | 0.00 | 95.30 | 0.10 | — |
| $NaBH_4$ | 0.91 | 6.80 | 0.80 | 56.60 | 32.70 | 0.00 |

EXAMPLE 6

(Not within the scope of the present invention.)

The ability of sodium borohydride to activate triphenylborane as a catalyst for the disproportionation of cyclohexyldichlorosilane was evaluated. A mixture consisting of 2.0 ml of cyclohexyldichlorosilane, 0.03 g (1.5 Wt %) of triphenylborane, and 0.02 g (0.9 Wt %) of sodium borohydride was formed in a tube prepared as described in Example 3. The tube was sealed and heated for one hour at 130° C. At the end of one hour, the tube was cooled and the contents of the tube analyzed by GLC-FID. About 95.8 percent of the area under the GLC-FID trace was attributable to cyclohexyldichlorosilane, with the rest being unidentified. This example demonstrates the requirement for one or more aryls to be bonded to the silicon atom.

EXAMPLE 7

The ability of sodium borohydride to activate triphenylborane as a catalyst for the disproportionation of methylphenylchlorosilane was evaluated. The process was conducted in sealed tubes in a manner similar to that described in Example 3. Mixtures consisting of 2.0 ml of methylphenylchlorosilane and the concentrations of triphenylborane and sodium borohydride described in Table 7 were formed. The mixtures were heated in sealed tubes at 130° C. for one hour. At the end of the one hour heating period the mixture was cooled and analyzed by GLC-FID. The results are presented in Table 7 as the percent area under the GLC-FID trace for each of the listed compounds.

TABLE 7

Sodium Borohydride Activation of The Triphenylborane
Disproportionation of Methylphenylchlorosilane
in Sealed Tubes

| Catalyst | Activator | GLC-FID Area % | | | | |
|---|---|---|---|---|---|---|
| (Wt % $Ph_3B$) | ($NaBH_4$) | $MeH_2SiCl$ | $PhMeSiH_2$ | $PhMeHSiCl$ | $(PhMeHSi)_2O$ | $Ph_2MeSiCl$ |
| — | — | 0.08 | 0.15 | 94.50 | 1.96 | 0.13 |
| 1.5 | — | 0.12 | 0.09 | 92.96 | 0.91 | 2.08 |
| 1.5 | 1.1 Wt % | 0.96 | 1.23 | 85.20 | 0.94 | 5.08 |

EXAMPLE 8

The effect of the physical form of sodium borohydride on its ability to activate triphenylborane was evaluated. The sodium borohydride was evaluated as a powder purchased from Aldrich Chemical, Milwaukee, Wis.; crushed 8.0 mm pellets as previously described; and pulverized 8.0 mm pellets, having an average particle size less than about 1.0 mm. The process was conducted in sealed tubes in a manner similar to that described in Example 3. Mixtures consisting of 2.0 ml of phenyldichlorosilane and the concentrations of triphenylborane and sodium borohydride described in Table 8 were formed. The mixtures were heated in sealed tubes at 130° C. for one hour. At the end of the one-hour heating period, the mixtures were cooled and analyzed by GLC-TC. The results are presented in Table 8 as the percent area under the GLC-TC trace for each of the listed compounds.

TABLE 8

| Catalyst | Activator | Form of | GLC-TC Area % | | | |
|---|---|---|---|---|---|---|
| (Wt % $Ph_3B$) | (Wt % $NaBH_4$) | Activator | $PhH_2SiCl$ | $PhHSiCl_2$ | $Ph_2SiCl_2$ | $C_6H_6$ |
| 1.3 | 0.8 | powder | 0.00 | 94.4 | 1.50 | 1.62 |

TABLE 8-continued

| Catalyst (Wt % Ph$_3$B) | Activator (Wt % NaBH$_4$) | Form of Activator | GLC-TC Area % | | | |
|---|---|---|---|---|---|---|
| | | | PhH$_2$SiCl | PhHSiCl$_2$ | Ph$_2$SiCl$_2$ | C$_6$H$_6$ |
| 1.3 | 0.6 | pulverized | 0.00 | 93.8 | 0.00 | 0.70 |
| 1.3 | 0.6 | crushed | 1.34 | 49.5 | 41.48 | 2.50 |

The data of Table 8 demonstrate that the pellet form of sodium borohydride is the preferred form.

What is claimed is:

1. A process for disproportionation of arylsilanes, the process comprising (A) forming a mixture comprising arylsilanes of formula $$R_aR^1_bH_cSiX_{4-a-b-c},$$

a phenylborane catalyst of formula $$Ph_nBX_{3-n},$$

and sodium borohydride activator, where concentration of the phenylborane catalyst is sufficient to increase rate of disproportionation of the arylsilanes and concentration of sodium borohydride is sufficient to reduce induction time for the process;

(B) heating the mixture to a temperature within a range of about 70° C. to 170° C.; and (C) recovering product silanes of formula $$R_{a+1}R^1_bH_{c-1}SiX_{4-a-b-c} \text{ and}$$
$$R_{a-1}R^1_bH_{c+1}SiX_{4-a-b-c};$$

where each R is independently selected from a group consisting of aryls and substituted aryls, $R^1$ is selected from a group consisting of alkyls of one to 20 carbon atoms, X is a halogen selected from a group consisting of bromine, chlorine, and iodine, Ph is phenyl, a=1, 2, or 3, b=0, 1, or 2, c=1, 2, or 3, a+b+c=2, 3, or 4, and n=1, 2, or 3.

2. A process according to claim 1, where R is phenyl.

3. A process according to claim 1, where $R^1$ is methyl.

4. A process according to claim 1, where the halogen is chlorine.

5. A process according to claim 1, where the arylsilane is phenyldichlorosilane.

6. A process according to claim 1, where the arylsilane is methylphenylchlorosilane.

7. A process according to claim 1, where the phenylborane catalyst is triphenylborane.

8. A process according to claim 1, where the concentration of the phenylborane catalyst is within a range of about 0.1 to 5.0 weight percent of the arylsilanes in the mixture.

9. A process according to claim 1, where the concentration of the sodium borohydride activator is within a range of about 0.5 to 2.0 weight percent of the arylsilanes in the mixture.

10. A process according to claim 1, where the sodium borohydride has a particle diameter within a range of about 1 mm to 12 mm.

11. A process according to claim 1, where the temperature is within a range of about 100° C. to 150° C.

12. A process according to claim 1, where the mixture is held at the temperature for about 15 minutes to one hour to effect disproportionation of the arylsilanes.

13. A process according to claim 1, where the product silane is diphenyldichlorosilane.

14. A process according to claim 1, where the product silane is methyldiphenylchlorosilane.

* * * * *